United States Patent [19]

Gold

[11] 4,194,291
[45] Mar. 25, 1980

[54] DENTAL TOOL

[76] Inventor: Henry O. Gold, 1250 Willow Rd., Winnetka, Ill. 60093

[21] Appl. No.: 901,687

[22] Filed: May 1, 1978

[51] Int. Cl.² ............................................ A61C 3/02
[52] U.S. Cl. ..................................................... 433/75
[58] Field of Search ................................ 32/12, 49, 29

[56] References Cited

U.S. PATENT DOCUMENTS

| 1,480,730 | 1/1924 | Lentz | 32/49 |
| 2,176,339 | 10/1939 | Henneman | 32/49 |
| 3,600,810 | 8/1971 | Marshall | 32/49 |

Primary Examiner—Robert Peshock
Attorney, Agent, or Firm—Dressler, Goldsmith, Clement, Gordon & Sho re, Ltd.

[57] ABSTRACT

A dental instrument for preparing a tooth for receiving a crown in an area not visible to the dentist which includes a guide member disposed adjacent to the cutting instrument and is freely rotatable relative to the cutting instrument. The guide surrounds the cutting instrument and includes at its lower end a shield that prevents the cutting instrument from contacting the surrounding gum. The guide limits the horizontal depth of cut and vertical depth of cut into the tooth during the tooth preparation.

2 Claims, 5 Drawing Figures

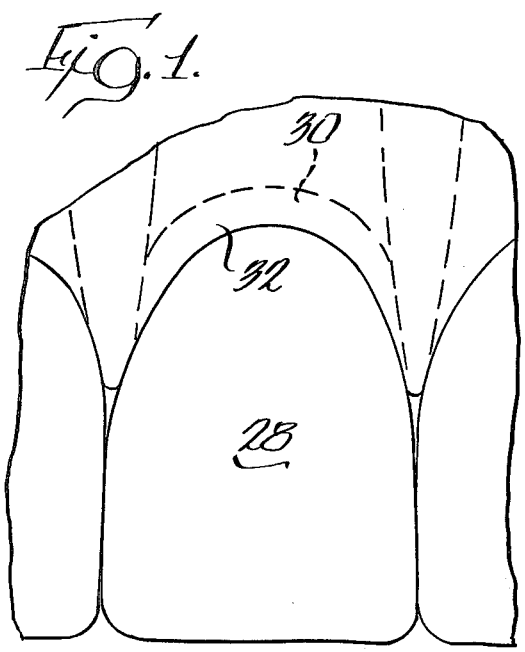
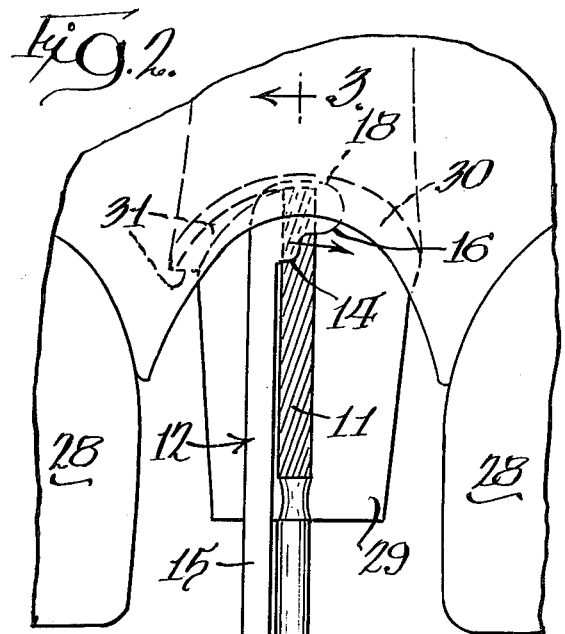
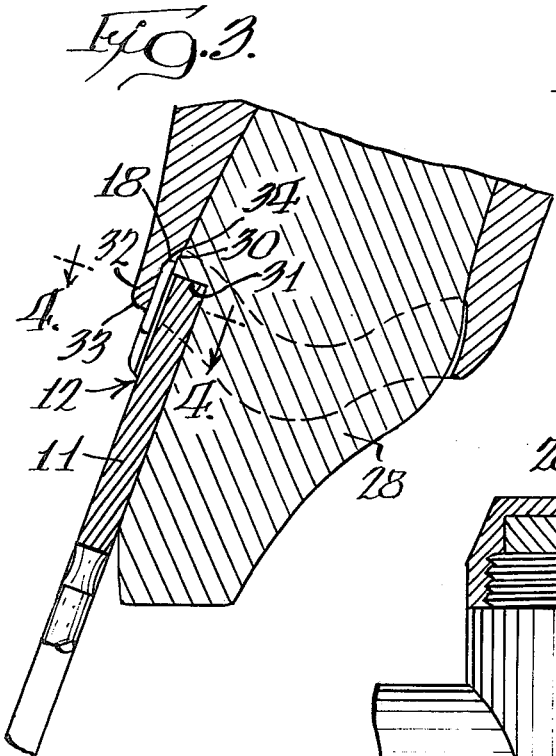
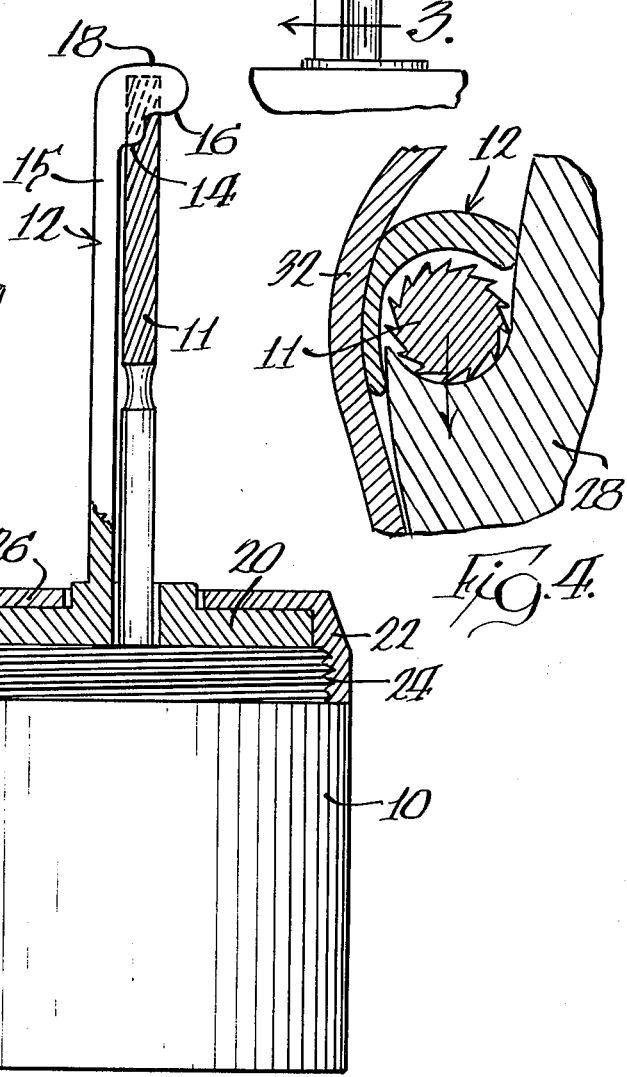

DENTAL TOOL

This invention relates to a dental tool, and, particularly, to one that is used to prepare a tooth to receive a tooth coverage in an area not normally visible to the dentist, and is the single most difficult procedure to perform in tooth preparation.

In preparing a tooth to receive a tooth coverage, such as a crown, it is most often desirable to make such tooth preparation in an area that is not normally visible to an observer. A tooth preparation, such as a shoulder, bevel, chamfer, or slice, is usually performed adjacent the cervical or gingival area of the tooth, which is that portion of the tooth near the junction of the crown and root, or the gum line. The cervical line of the tooth is normally covered over by what is commonly known in dental parlance as the gingiva and in every day language is referred to as the gums. However, the gingiva is by definition the fibrous tissue covered by mucous membrane that immediately surrounds the tooth. The portion surrounding the crown of the tooth is free and can be serially retracted away from the tooth, and this is normally referred to as the free gingiva. Currently, when, for example, a shoulder is to be cut into the tooth which is to be done subgingivally, which is that area within the groove formed between the gingiva and the tooth, there is no assurance that the shoulder will be formed in a uniform manner around the circumference of the tooth. Of great concern is also the damage that may be done to the surrounding gum, since when working on the tooth subgingivally, it is practically impossible to avoid abrading the gums and causing undesirable and sometimes irreversible damage to the overlying gum tissue. As presently practiced, the formation of the shoulder with controlled depth of cut into the tooth and distance below the gum margin with the minimizing of damage to the surrounding soft tissues taxes the skill of even the more sophisticated operator, since often this procedure is being carried out in an unvisualized area with water coolant spraying and the gum bleeding.

This problem has long been recognized and mechanisms have been developed that have not met with commercial success due to their lack of feasibility. One such example is that shown and described in French Pat. No. 2,249,645, which discloses a complex, cumbersome tool that is capable of preventing abrasion in one located area, but clearly cannot function to form a shoulder, or the like, circumferentially and in particular not on the facial surface of anterior teeth, which is the primary area where this procedure is necessary, while following the contour of the gum line at the desired distance under the gum within the crevice. It has a non-rotatable guard, which precludes the possibility of utilization over more than about one-half the circumference at the gingival area.

It can be seen that it would be a giant step forward in the field of dentistry if there was an instrument available that would enable the operator to form a shoulder or other type of tooth preparation of uniform depth and properly place it to follow the contour of the gum line at the desired distance under the gum within the crevice, and yet minimize, if not completely eliminate the possibility of abrading the adjacent gum portion during the preparation of the tooth. If, in addition, the tool could serve to limit the horizontal and vertical depths of cut into the tooth, it would be highly advantageous. With such a tool, every dentist would become a highly skilled operator when preparing a tooth to receive a tooth coverage which terminates subgingivally.

In accordance with the present invention, there is provided a novel dental tool which will insure that the tooth preparation that takes place, whether it be a shoulder, chamfer, or slice, etc., be done at a uniform depth about the selected portion of the tooth and that there be provided a contour guide and shield that aids in guiding the cutting instrument about the tooth while shielding the adjacent gum portion from the cutting instrument to eliminate abrading of the surrounding tissue during the tooth preparation. The guide will also serve to limit the depth of cut in both the horizontal and vertical directions during the tooth preparation.

In essence, the invention consists of a freely rotatable guide mechanism which has a blunt tip arrangement adapted to be slipped into the crevice formed between the free gum and the tooth. The guard portion adjacent to the tip is graduated in such a manner as to visually indicate the distance within the crevice and below the gum margin the guide guard and rotary cutting instrument is being carried. The base of the crevice surrounding the tooth is technically referred to as the gingival attachment, which is where the gingival tissue attaches to the teeth. The blunt tip of the guide is so designed that if one wishes to use the bottom of the crevice as a reference area when carrying the preparation circumferentially it can be done. However, the crest of the free gingiva can be used as the reference margin and the depth of penetration of the instrument be measured from that point. In addition, the guide-guard tip can be designed with a section which embraces the gum margin or crest to aid as an axial direction stop and guide.

The novel guide and guard forming the instant invention is designed to at least partially surround the rotary cutting instrument and is free to rotate relative thereto. Thus, as the cutting instrument is moved around the cervical area of the tooth, the guide which is freely rotatable can be maintained in position between the cutting instrument and the surrounding gum, with the result that a uniform shoulder, bevel, etc., will be formed, as desired, and the cutting instrument or bur in this case will be prevented from contacting the gum and causing abrasion resulting in bleeding, and laceration to the overlying gum tissue. Also, the guide guard is designed so that it limits the horizontal and vertical movement of the bur and thus limits the horizontal and vertical depths of cut of the tooth.

The invention can be more particularly understood from a review of the attached drawings, in which:

FIG. 1 is a partial view of teeth and surrounding gum;

FIG. 2 is a view showing the novel depth and contour guide in position during the tooth preparation;

FIG. 3 is a view taken along line 3—3 of FIG. 2;

FIG. 4 is a view taken along line 4—4 of FIG. 3; and

FIG. 5 is a view of the novel depth and contour guide shown mounted on a turbine handpiece instrument.

Referring first to FIG. 5, it is seen that the invention is used in conjunction with turbine-driven instrument 10 which in the instant case will be shown in conjunction with a bur 11. Rotary instruments of various types can be used. Also, different shaped guide and guard arms to accommodate for various shaped rotary cutting instruments can be inserted as required. The design of the basic instrument, whether it be the conventional type, or merely a cylindrical housing, is not critical to the invention. Of course, other cutting instruments can be used, such as, a mounted diamond point, steel or carborundum bur, etc.

The novel depth and contour guide is generally indicated by the numeral 12 and in the configuration shown has disposed at the lower end thereof indicia marks 14, 16, which will indicate the depth of the guide below the crest of the gingiva when it is inserted in place to prepare a tooth. The lower end of the guide includes a blunt tip 18 which, if desired, can be rested against the bottom of the crevice in which it is to be located, while the bur 11 is performing the desired action on the tooth. It can be seen that the blunt tip portion 18 is located below the tip of the bur 11 and acts as a positive stop to limit the depth of cut into the side or axial wall of the tooth. Blunt tip portion 18 of the guide 12 limits the horizontal depth of cut into the tooth. The sidewall 15 tends to keep the guide guard turning as the cut is carried circumferentially.

In FIG. 5, the guide is shown as being affixed relative to the turbine instrument 10 by a housing 22 which is threaded at 24 to the instrument 10. The portion of the guide 12 affixed to the instrument includes an annular flange 20 which abuts an inwardly extending annular flange portion 26 of the housing 22. This acts as a bearing to allow 360° rotation of the guard guide extension. Thus, it can be seen that the guide is positively located relative to the instrument, but is free to rotate relative thereto guided by the end of the guide guard following in the crevice and assisted in rotating by the turbine effect created by the rotating cutting instrument spinning close to the long axial arm of the guide guard with the coolant water interposed, or by mere hand manipulation against the side of the guide 12.

The most difficult procedure to accomplish in full coverage tooth preparation is the creation of a subgingival shoulder of even depth and proper cervical contour. This instrument makes it possible to accomplish both depth and cervical contour in a precise manner, which is not possible to duplicate in the heretofore conventional free-hand method. This instrument makes this procedure fast, simple, and precise when in the hands of clinicians of even very modest skill. This device should improve the services in crown and bridge procedures offered the public by increasing efficiency, function, esthetics, economy, and longevity of this type prostheses.

Referring to FIGS. 1-4, it is shown how the novel depth and contour guide performs its function. FIG. 1 illustrates a plurality of teeth with the dashed lines adjacent the base of the center tooth 28 indicating the bottom of the crevice 30 into which the depth and contour guide is to be inserted.

In FIG. 2, there is shown the depth and contour guide extending into the crevice 30 to form the gingival and cervical area of the tooth preparation which in this case is a shoulder, as indicated by the dotted lines 31. A portion of the tooth has been cut away to the configuration shown at 29 by another appropriate instrument prior to the creation of the subgingival shoulder. A cross section of this view shown in FIG. 3 more clearly illustrates the relative position between the bur and depth and contour guide when forming the shoulder 31 heretofore referred to in FIG. 3. It can be seen that the guide has pushed away the gingiva 32 and serves as a guard between the bur 11 and gingiva 32 to prevent damage to the gum during the tooth preparation. An enlarged view of the relationships between the free gingiva 32, guide 12, bur 11 and tooth 28 is shown in FIG. 4.

During the actual tooth preparation in the subgingival area, the depth and contour guide is interposed below the crest 33 of the free gingiva portion 32, which is free to be serially retracted relative to the tooth and moves it aside to permit the guide and associated bur to be moved into the crevice 30 to the preselected depth where the tooth is to be prepared by the bur 11. The guide will be moved axially for the desired distance relative to the crest of the gingiva as visualized by the graduations on the guards or until it engages the bottom of the crevice 30, which is technically referred to as the gingival attachment 34. The free gingiva portion essentially surrounds the tooth and the guide will be moved circumferentially around the tooth while being braced positively against the tooth to make the desired cut on the tooth. Thus, once the relationship between the guide and the bur is established, and the guide is introduced into the crevice, the operator will be able to form a uniform depth of cut around the tooth with the proper contour in an area which is not clearly visible to the operator.

Of importance is that during the cutting action the gingiva, or gum, will be protected from the cutting tool by the guard, which thus eliminates abrasion thereof.

It can be appreciated that the guide can take many forms and various types of designs could be used to meet whatever requirements the operator might have. As aforementioned, the freedom of rotation of the guide relative to the instrument gives the operator the opportunity to move the guide 360° around the long axis of the rotary cutting instrument as the tooth preparation is carried circumferentially.

This invention should greatly improve the services the general dentist is able to perform for patients requiring crowns and fixed partial denture prostheses. Heretofore, these prostheses were often avoided, or poorly executed, to the detriment of patient care, because of the high degree of dexterity required to adequately perform this procedure. With this instrument, every dentist can have the required expertise.

It is, of course, intended to cover by the appended claims all such improvements and modifications as fall within the true spirit and scope of the invention.

What is claimed is:

1. A dental instrument for preparing the gingival or cervical area of a tooth for receiving a tooth coverage, or crown, consisting of a rotary driven cutting instrument, a guide disposed adjacent to said cutting instrument and freely rotatable relative thereto, said guide surrounding a portion of said cutting instrument and defining at its lower end a shield which prevents the cutting instrument from contacting that which is protected by said shield, and a guide that limits the horizontal depth of cut and the vertical depth of cut into the tooth providing a uniformly prepared surface, the guide further defining indicia means at its lower end to clearly indicate the depth of penetration of said guide when the tool is used to prepare a tooth below the gum crest, said guide also defining a blunt end portion adapted to contact the bottom of the crevice and rest positively against the tooth surface beyond the rotary cutting instrument in which the guide is located to define the limit of penetration of said guide, both in an axial and horizontal direction.

2. A dental instrument of the type set forth in claim 1 in which the guide is retained in place relative to the instrument by a member connected thereto, said member supporting said guide so it is free to rotate relative to said instrument, whereby the guide can be readily rotated 360° to maintain it between the gum and the tooth as the cutting instrument is moved around the tooth.

* * * * *